United States Patent [19]
Horner

[11] 4,010,357
[45] Mar. 1, 1977

[54] ANALOG VISIBILITY COMPUTER

[75] Inventor: Joseph L. Horner, Cambridge, Mass.

[73] Assignee: The United States of America as represented by the Secretary of the Department of Transportation, Washington, D.C.

[22] Filed: Dec. 8, 1975

[21] Appl. No.: 638,599

[52] U.S. Cl. .................... 235/151.3; 356/103
[51] Int. Cl.² ............... G01V 1/28; G01N 21/00
[58] Field of Search ....... 235/151.3, 150.2, 150.22, 235/184, 185; 356/103, 201, 204, 229, 104, 227, 218, 205; 250/265

[56] References Cited

UNITED STATES PATENTS

| | | | |
|---|---|---|---|
| 3,501,239 | 3/1970 | Rouet | 356/103 |
| 3,510,225 | 5/1970 | Collis | 356/103 |
| 3,519,354 | 7/1970 | Brown, Jr. et al. | 356/103 |
| 3,651,252 | 3/1972 | Land et al. | 356/229 |
| 3,668,674 | 6/1972 | Westendorf | 356/103 |
| 3,745,350 | 7/1973 | Hill et al. | 356/208 |
| 3,746,452 | 7/1973 | Teboul et al. | 356/201 |
| 3,758,211 | 9/1973 | Bateman et al. | 356/103 |
| 3,782,824 | 1/1974 | Stoliar et al. | 356/103 |
| 3,788,745 | 1/1974 | Menke | 356/204 |

OTHER PUBLICATIONS

Instruments for the Measurement of the Visual Range; Beuttell et al; Journal of Scientific Instruments; Nov. 1949; vol. 26 pp. 357–359.
Harrower; Runway Visual Range, Slant Visual Range and Meteorological Visibility; Meteorological Magazine (British); Jan, 1963 pp. 26–34.

Primary Examiner—Charles E. Atkinson
Assistant Examiner—Errol A. Krass
Attorney, Agent, or Firm—Herbert E. Farmer; Harold P. Deeley, Jr.

[57] ABSTRACT

The computation of visual range is performed by a compact and comparatively inexpensive analog circuit which receives, as primary input information, a signal corresponding to atmosphere extinction coefficient. The circuit simultaneously solves Allard's and Koshmieder's equations and provides an output voltage, corresponding to the instantaneous visual range, by sampling the output of a ramp voltage generator upon solution of both equations.

14 Claims, 2 Drawing Figures

ANALOG VISIBILITY COMPUTER

ORIGIN OF THE INVENTION:

The invention described herein was made by an employee of the United States Government and may be manufactured and used by or for the Government for governmental purposes without the payment of any royalties thereon or therefor.

BACKGROUND OF THE INVENTION:

1. Field of the Invention

The present invention is directed to a technique for computing the distance an observer may be from an object or source of illumination and still see that object or source. More specifically, this invention relates to apparatus for calculating visual range. Accordingly, the general objects of the present invention are to provide a novel and improved method and apparatus of such character.

2. Description of the Prior Art

The guidance of all transportation vehicles is intimately related to the ability of a human operator to clearly see the pathway ahead of the vehicle and maneuver the vehicle appropriately. As traffic volumes and speeds increase, there is a concommitant increase in the need for improved apparatus for accurately measuring visibility through the atmosphere. Such apparatus could find utility in assisting the guidance of land and naval vehicles as well as aircraft. Considering the environment of an aircraft, it is necessary to provide the pilot with information as to how far he can see runway lights and similar information must be provided to the ground controllers so that they will know when the local visibility conditions require the closing of a runway.

Techniques for computing runway visual range (RVR) and apparatus for use in the implementation of such techniques are presently known. However, all previously proposed or available apparatus have the limitation that they do not directly measure human visibility. Thus, prior art devices for use in visual range measurement; as exemplified by U.S. Pat. Nos. 3,510,225, 3,519,354, 3,745,350, 3,746,452 and 3,782,824; provide output information in the form of the atmospheric extinction coefficient. This parameter is not easily interpreted by human observers and thus is not particularly useful in informing a pilot or driver, respectively, as to how far he can see a certain visual clue such as, for example, landing lights or highway markers.

Many airports presently employ a system for assessing visibility which includes a runway visual range transmissometer. The system presently approved by the Federal Aviation Administration employs a field sensor, which includes a light source and receiver spaced 250 feet apart, placed adjacent to the runway. The field sensor measures the atmospheric transmittance, of the fixed 250 foot path. The atmospheric transmittance which may be expressed as the extinction coefficient of the atmosphere, is employed as an input to an expensive, large and immobile digital computer. The digital computer is programmed to provide an output which represents the distance that an average pilot can see runway edge lights under the prevailing atmospheric transmittance conditions. In accomplishing this objective the computer will solve two physchophysical equations in order to convert the extinction coefficient or atmospheric transmittance to visual range. The first of these equations is Allard's law which may be expressed as follows:

$$E_t = \frac{I_o (t_b)^{R/b}}{R^2} \quad (1)$$

where:

$E_t$ is the illuminance threshold; i.e., a property of the eye and the background lighting conditions;

$I_o$ is the luminous intensity of the specific target light (the runway edge lights, for example);

$t_b$ is the atmospheric transmittance measured over a path length b (the distance between the light source and receiver of the field sensor); and R is the visual range. The visual range is also computed using Koshmieder's law which may be expressed as follows:

$$C_R = C_o (t_b)^{R/b} \quad (2)$$

where:

$C_o$ is the contrast of a target; and $C_R$ is the observed contrast. The limiting value of the contrast threshold is taken to be 5.5% for aviation purposes. The digital computer solves both equations for R and selects the larger visual range value for display. In performing its function the digital computer in the present FAA transmissometer is essentially a loop-up table where pre-computed value pairs of $t_b$ and runway visual range are stored. The necessity of employing an expensive and essentially immobile digital computer to calculate, from input information in terms of the extinction coefficient of the atmosphere, the instantaneous visual range has precluded the widespread provision of visual range information to vehicle operators and, in the case of aircraft, has limited runway visual range determination to those airports having commercial service, to the detriment of the general aviation community.

SUMMARY OF THE INVENTION:

The present invention overcomes the above-briefly discussed and other deficiencies and disadvantages of the prior art by providing a novel technique for the computation of visual range. The present invention also contemplates apparatus for use in the practice of such technique characterized by reliability, accuracy, comparatively moderate cost and sufficiently small size and weight to impart potential portability thereto. Thus, in accordance with the present invention there is provided an analog visibility computer for solving, from input information commensurate with the atmospheric extinction coefficient, an output signal corresponding to the instantaneous visual range for the existing atmospheric and lighting conditions.

Apparatus in accordance with the present invention includes a ramp voltage generator and a pair of computation circuits. Employing an input signal from a field sensor commensurate with the atmospheric extinction coefficient, the Allard's law and Koshmieder computations are performed simultaneously and an output signal is generated when both equations have been solved. This output signal is employed to terminate rise of the ramp voltage whereby the output voltage of the ramp voltage generator will correspond to the larger of the two calculated visual range values. The output voltage of the ramp voltage generator is, upon solution of the two equations, applied to a sample and hold circuit and the output of the sample and hold circuit is, in turn, displayed as an output voltage proportional to the visual rage. The Allard's law computation circuit includes a plurality of bias voltage selectors which permit adjustment of the constants in the equation for day and night background lighting conditions. The Allard's law computation circuit may also include adjustable bias voltage sources which provide compensation, in the case of a runway visual range embodiment, for the instantaneous runway light intensity setting.

BRIEF DESCRIPTION OF THE DRAWING:

The present invention may be better understood and its numerous objects and advantages will become apparent to those skilled in the art by reference to the accompanying drawing wherein.

DESCRIPTION OF THE PREFERRED EMBODIMENT:

In the operation of the embodiment of FIG. 1, the Allard's law equation is rewritten in a consistent set of units as follows:

$$E_t = \frac{I_o (t_b)^{R/b}}{(R/5280)^2} \qquad (3)$$

where $E_t$ is in units of mile-candles, R is in feet and $I_o$ is in candelas. To find the visual range, equation (3) is solved for the transcendental variable R. Taking the common logarithm of both sides of equation (3) and rearranging terms, the Allard's law equation may be expressed as follows:

$$\log\left(\frac{E_t}{I_o (5280)^2}\right) = \frac{R}{b} \log t_b - 2 \log R \qquad (4)$$

As should be obvious, the left side of equation (4) contains only fixed parameters and the right side of the equation contains the running variable R and the output of the field sensor $t_b$; the atmospheric extinction coefficient $t_b$ being expressed as a fraction which is always less than one.

For a runway visibility range implementation, the Koshmieder's law equation (2) may also be rewritten, with $C_R/C_o$ set as equal to 0.055, as follows:

$$-1.260 = \frac{R}{b} \log t_b \qquad (5)$$

Figure 1:
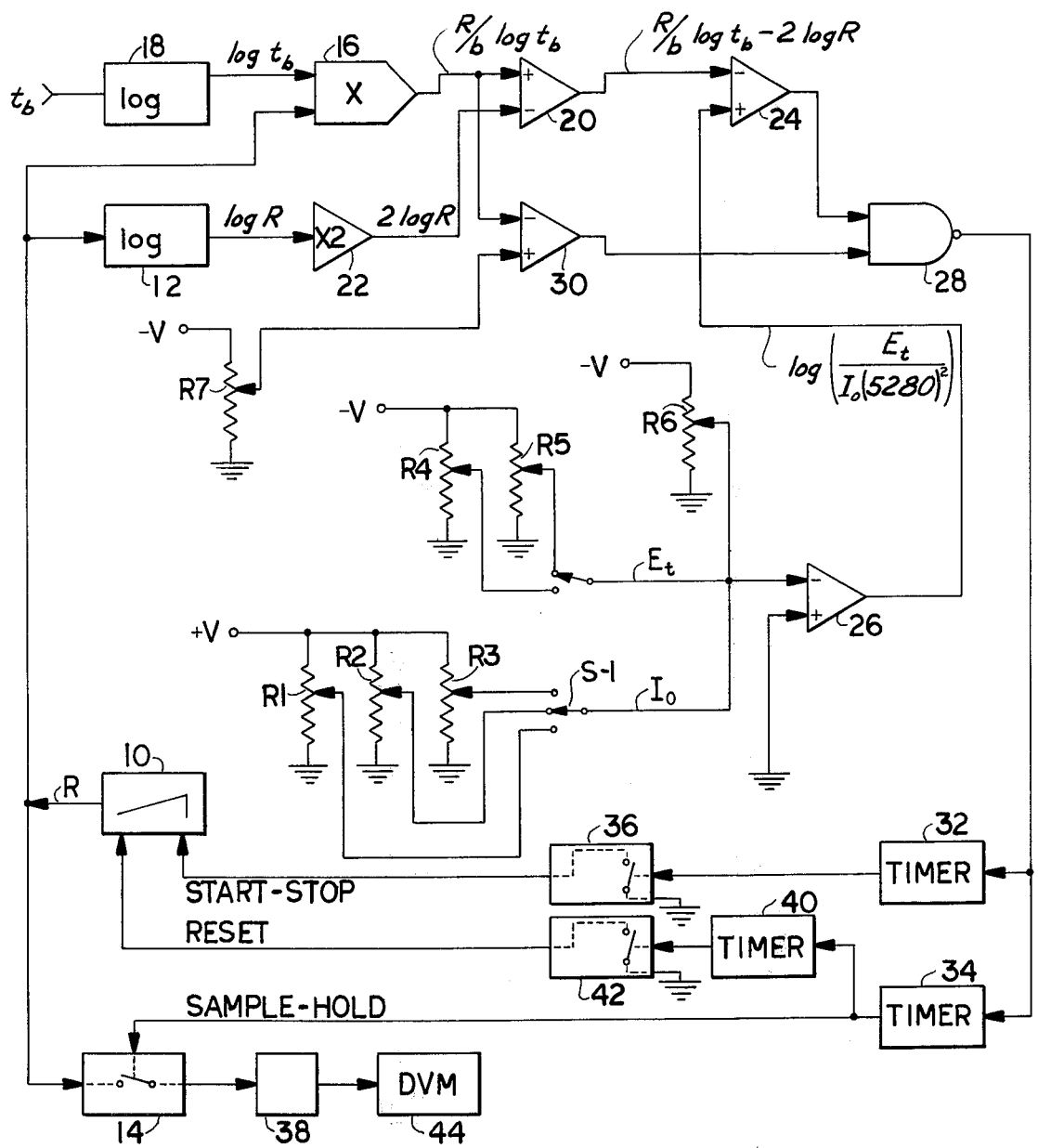
FIG. 1 is a functional block diagram of an analog computer in accordance with a preferred embodiment of the invention.
Figure 2:
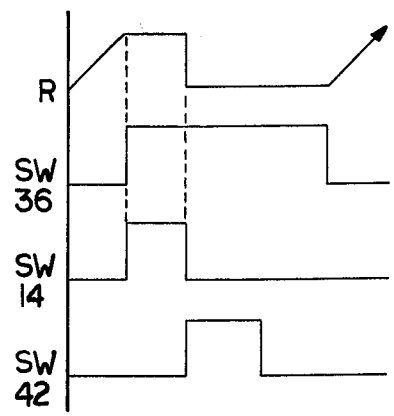
FIG. 2 is a timing sequence diagram pertaining to the embodiment of FIG. 1.

With reference now jointly to FIGS. 1 and 2, a ramp voltage generator, which produces a linearly increasing output voltage R, is indicated at 10. The output of ramp voltage generator 10 is applied as the input to a logarithmic amplifier 12. The output of ramp voltage generator 10 is also applied as an input to a solid state switch 14 and as a first input to a multiplier 16. A signal commensurate with the atmospheric extinction coefficient $t_b$, as provided by a field sensor, is applied as an input to a second logarithmic amplifier 18. The voltage R and the logarithm of the atmospheric extinction coefficient, appearing at the output of amplifier 18, are multiplied in multiplier 16 and the product is applied as an input to an operational amplifier 20 which performs a subtraction function.

The log R output of logarithmic amplifier 12 is applied as an input to a linear amplifier 22, having a gain of 2, and the 2 log R output signal of amplifier 22 is applied as a second input to operational amplifier 20. The output of operational amplifier 20, corresponding to $(R/b \log t_b - 2 \log R)$, is applied as a first input to a comparator 24.

The second input to comparator 24 is the constant quantity which forms the left hand side of equation (4) above. This quantity is derived via a plurality of variable resistances. Thus, a first input to a further operational amplifier 26 is derived by selecting one of the signals appearing at the wiper arms of a first of three potentiometers R1, R2 and R3. The potentiometers R1, R2 and R3 will be included only when the apparatus forms part of a runway visual range computer and these potentiometers will be preset in accordance with the runway light intensity $I_o$ settings which may be selected by a ground controller. The selection of which of potentiometers R1, R2 and R3 will have its wiper arm connected to provide the first input to amplifier 26 normally is accomplished automatically along with the setting of the runway light intensity. The second; i.e., the $E_t$; input to amplifier 26, which is summed at the amplifier input terminals with the runway light intensity setting input, is derived from one of a pair of further variable resistances R4 and R5. The variable resistances R4 and R5 are respectively set to provide input signals commensurate with the background lighting conditions; potentiometer R4 being the night setting and potentiometer R5 being the day setting. In the current FAA system, the day setting of $E_t$, as derived from the wiper arms of either of potentiometers R4 or R5, is taken to be 1000 mile-candles and the night setting is take to be 2 mile-candles. It will be understood that the present invention contemplates the alternative use of a photocell or other suitable sensor to continuously monitor the background of lighting conditions and to provide an input signal to amplifier 26 commensurate with log $E_t$. It will also be understood that potentiometers R1–R5 are scaled such that their output signals correspond to the logarithms of the quantities $I_o$ and $E_t$. A further potentiometer R6 provides additional input bias to amplifier 26 commensurate with the constant ($5280^2$) in the left side of equation (4). Amplifier 26 provides an output signal commensurate with:

$$\log\left(\frac{E_t}{I_o (5280)^2}\right)$$

As previously noted, the outputs of amplifiers 20 and 26 are applied as inputs to comparator 24. The output of comparator 24 will go high when the Allard's law equation has been solved; i.e., when both sides of equation (4) above are equal. The output signal indicating that the Allard's law equation has been solved is applied as a first input to a NAND gate 28.

A second input to NAND gate 28 will indicate that the Koshmieder's law equation has also been solved. This second input is derived from a further comparator 30 which receives, as inputs, the output of multipliers 16 and a constant bias signal, provided by potentiometer R7, commensurate with the constant 1.260. The output of NAND gate 28 will go low after both of equations (4) and (5), respectively commensurate with solution of the Allard's law and Koshmieder's law equations, have been solved; i.e., when the outputs of comparator 24 and comparator 30 both go high.

The output signal from NAND gate 28 is provided as an initiating input to a pair of timing circuits 32 and 34. The output of timer 32 controls, via a solid state switch 36, the starting and stopping of ramp voltage generator 10. The output of timer 34 controls, via the previously mentioned solid state switch 14, the application of the output of ramp voltage generator 10 to a sample and hold circuit 38. The output of timer 34 is also applied as an input to a further timer 40 which controls, via its associated solid state switch 42, the resetting of ramp voltage generator 10. As may be seen from the timing diagram comprising FIG. 2, timers 32 and 34 cause the simultaneous closing respectively of switches 36 and 14 whereby the ramp voltage output of generator 10 is, upon the generation of an output signal by NAND gate 28, caused to stop increasing; i.e., the integration function of ramp voltage generator 10 is terminated; and the steady state voltage appearing at the output of the ramp voltage generator upon the "firing" of gate 28 is applied to sample and hold circuit 38. As will be obvious, timers 32 and 34 may be monostable multivibrators having different periods; the period of timer 34 being less than that of timer 32. Timer 40, which may also comprise a monostable circuit, is responsive to the trailing edge of the output of timer 34. The closing of switch 42, which causes the resetting of ramp voltage generator 10, will thus occur after the opening of sample-hold switch 14. Subsequent to resetting of the ramp voltage generator, timer 32, will, via solid state switch 36, permit the output of ramp voltage generator 10 to again begin increasing.

The output of sample and hold circuit 38 will be applied to a digital voltmeter 44 or other suitable display device. The voltage level at which the R output of ramp voltage generator 10 was stopped by the output of gate 28 will be scaled to be commensurate with the runway visual range in feet and this visual range may be read directly from the display of voltmeter 44. The presence of sample and hold circuit 38 prevents the display provided by voltmeter 44 from flickering during the computation cycle. Thus, if a change in $t_b$ does not occur from one cycle to the next, the display will not change its indicated visual range value but rather will show a steady non-changing value.

While a preferred embodiment has been shown and described various modifications and substitutions may be made thereto without departing from the spirit and scope of the invention. Accordingly, it is to be understood that this invention has been described by way of illustration and not limitation.

What is claimed is:

1. Apparatus for providing an indication of visual range comprising:
    means for generating a voltage which varies with time from a predetermined level, said varying voltage generating means being resettable to said predetermined level;
    first circuit means connected to said voltage generating means and responsive to an input field sensor measured signal commensurate with the instantaneous atmospheric transmittance and to said varying voltage for computing visual range as a function of a constant existing illuminance threshold and a constant luminous intensity of a preselected object, said first circuit means providing an output signal when the magnitude of said varying voltage reaches a level commensurate with the computed visual range;
    second circuit means responsive to said input signal commensurate with the instantaneous atmospheric transmittance and to said varying voltage for computing visual range as a function of a constant contrast of the preselected object and a constant observed contrast, said second circuit means providing an output signal when the magnitude of said varying voltage reaches a level commensurate with the computed visual range;
    logic circuit means connected to said voltage generating means and to said first and second circuit means, said logic circuit means being responsive to the output signals provided by said first and second circuit means for terminating variation of the magnitude of the output voltage of said voltage generating means when both of said first and second circuit means provide output signals; and
    means for sampling the output of said voltage generating means when the variation in magnitude thereof is terminated whereby said sampling means will measure a voltage commensurate with the greater of the visual ranges as computed by said first and second circuit means.

2. The apparatus of claim 1 wherein said first circuit means solves Allard's equation.

3. The apparatus of claim 2 wherein said second circuit means solves Koshmieder's equation simultaneously with the solution of Allard's equation by said first circuit means.

4. The apparatus of claim 1 wherein said first circuit means solves the expression:

$$\log\left(\frac{E_t}{I_0(5280^2)}\right) = \frac{R}{b}\log t_b - 2\log R$$

where $t_b$ is measured atmospheric transmittance, $E_t$ is the constant background illuminance threshold expressed in units of mile-candles, $I_0$ is the constant luminous intensity of the preselected object expressed in candelas, and R is the visual range in feet.

5. The apparatus of claim 4 where the voltage measured by said sampling means is commensurate with runway visual range and wherein said second circuit means solves the expression:

$$-1.260 = \frac{R}{b}\log t_b$$

6. The apparatus of claim 5 further comprising:
    means connected to said logic circuit means and responsive to the sampling of the output of said voltage generating means for resetting said voltage generating means after a predetermined time delay.

7. The apparatus of claim 6 further comprising:

means coupled to said first circuit means for providing an adjustable voltage corresponding to the constant $E_t$ whereby said first circuit means provides compensation for varying background lighting conditions.

8. The apparatus of claim 7 further comprising:
means coupled to said first circuit means for providing an adjustable voltage corresponding to the constant $I_o$ whereby said first circuit means provides compensation for variations in the luminous intensity of the preselected target object.

9. The apparatus of claim 6 further comprising:
means coupled to said first circuit means for providing an adjustable voltage corresponding to the constant $I_o$ whereby said first circuit means provides compensation for variations in the luminous intensity of the preselected target object.

10. The apparatus of claim 1 further comprising:
means connected to said logic circuit means and responsive to the sampling of the output of said voltage generating means for resetting said voltage generating means after a predetermined time delay.

11. The apparatus of claim 1 wherein said first circuit means includes:
means for providing an adjustable input voltage commensurate with the constant illuminance threshold whereby the larger of the two computed visual ranges will be compensated for varying lighting conditions.

12. The apparatus of claim 11 wherein said first circuit means includes:
means for providing an adjustable input voltage commensurate with the constant luminous intensity whereby the larger of the two computed visual ranges will be compensated for variations in the luminous intensity of the preselected object.

13. The apparatus of claim 12 further comprising:
means connected to said logic circuit means and responsive to the sampling of the output of said voltage generating means for resetting said voltage generating means after a predetermined time delay.

14. The apparatus of claim 1 wherein said first circuit means includes:
means for providing an adjustable input voltage commensurate with the constant luminous intensity whereby the larger of the two computed visual ranges will be compensated for variations in the luminous intensity of the preselected object.

* * * * *